US012788430B2

(12) United States Patent
Chen et al.

(10) Patent No.: US 12,788,430 B2
(45) Date of Patent: Nov. 10, 2026

(54) NEEDLE GUIDE ASSEMBLY AND METHOD OF OPERATING THE SAME

(71) Applicant: Biobot Surgical Pte Ltd, Singapore (SG)

(72) Inventors: Hong Jun Chen, Singapore (SG); Jia Yun Hee, Singapore (SG); Lan Eng Poh, Singapore (SG); Guoyu Qian, Singapore (SG); Yew Tong Tan, Singapore (SG)

(73) Assignee: Biobot Surgical Pte Ltd, Singapore (SG)

( * ) Notice: Subject to any disclaimer, the term of this patent is extended or adjusted under 35 U.S.C. 154(b) by 832 days.

(21) Appl. No.: 17/420,298

(22) PCT Filed: Nov. 28, 2019

(86) PCT No.: PCT/SG2019/050585

§ 371 (c)(1),
(2) Date: Jul. 1, 2021

(87) PCT Pub. No.: WO2020/145889

PCT Pub. Date: Jul. 16, 2020

(65) Prior Publication Data

US 2022/0087710 A1 Mar. 24, 2022

(30) Foreign Application Priority Data

Jan. 11, 2019 (SG) ............................ 10201900302S

(51) Int. Cl.
*A61B 17/34* (2006.01)
*A61B 34/37* (2016.01)

(52) U.S. Cl.
CPC .......... *A61B 17/3403* (2013.01); *A61B 34/37* (2016.02); *A61B 2017/3405* (2013.01)

(58) Field of Classification Search
CPC ................ A61B 17/3403; A61B 34/37; A61B 2017/3405; A61B 90/11;
(Continued)

(56) References Cited

U.S. PATENT DOCUMENTS

| | | | | |
|---|---|---|---|---|
| 6,582,451 | B1 * | 6/2003 | Marucci | A61B 17/29 606/207 |
| 2009/0171203 | A1 * | 7/2009 | Avital | A61B 90/11 606/130 |

(Continued)

FOREIGN PATENT DOCUMENTS

| | | | |
|---|---|---|---|
| EP | 3908217 B1 | 11/2021 |
| JP | S63-299834 A | 12/1988 |
| WO | WO-2015052718 A1 | 4/2015 |

OTHER PUBLICATIONS

Definition of Translational motion (Year: 2025).*
(Continued)

*Primary Examiner* — Kathleen S Holwerda
*Assistant Examiner* — James R Mcginnity
(74) *Attorney, Agent, or Firm* — Harness, Dickey & Pierce, P.L.C.

(57) ABSTRACT

A needle guide assembly and an automated method of operating a needle guide assembly are provided. The assembly includes a needle guide body and a controller communicatively coupled to the needle guide body. The needle guide body includes at least two separable portions. The needle guide body is operable by the controller to actuate between a closed configuration and an open configuration. In the closed configuration, the at least two portions combine to define a channel therethrough for receiving a needle. In the open configuration, the at least two portions separate to release the received needle from the channel.

9 Claims, 5 Drawing Sheets

(58) Field of Classification Search
CPC .... A61B 2017/3409; A61B 2017/3407; A61B 17/3415; A61B 34/00; A61B 34/30; A61B 34/31; A61B 34/32; A61B 34/33; A61B 34/34; A61B 34/35; A61B 34/36; A61B 34/70; A61B 34/71; A61B 17/3468
See application file for complete search history.

(56) References Cited

U.S. PATENT DOCUMENTS

| | | | | |
|---|---|---|---|---|
| 2012/0265051 | A1* | 10/2012 | Fischer | A61B 34/37<br>73/800 |
| 2014/0128890 | A1 | 5/2014 | Kappel et al. | |
| 2016/0074063 | A1 | 3/2016 | Arimitsu et al. | |
| 2017/0020623 | A1* | 1/2017 | Glossop | A61B 18/1477 |
| 2019/0099587 | A1* | 4/2019 | Williams | A61B 17/3403 |
| 2020/0113613 | A1* | 4/2020 | Medina | A61B 8/461 |
| 2020/0121287 | A1* | 4/2020 | Nakamura | A61B 90/11 |
| 2020/0352672 | A1* | 11/2020 | Chu | A61B 17/3403 |

OTHER PUBLICATIONS

International Search Report and Written Opinion of the International Searching Authority, issued in PCT/SE2019/050585, mailed Jan. 28, 2020; ISA/SG.
European Search Report for Application No. 19 908 154.8-1113 dated Jan. 1, 2024 (7 Pages).
Written Opinion from the Intellectual Property Office of Singapore for Application No. 10201900302S, dated Apr. 18, 2023 (8 pages).
Extended European Search Report for Application No. 19908154.8 dated Aug. 19, 2022.
First Office Action from the China National Intellectual Property Administration for Application No. / Patent No. 1 2019800886935 / Issue serial No. 2023112900006550, Issue Date: Nov. 29, 2023 (23 Pages).
Examination Report No. 1 For Standard Patent Application No. AU2019420611 by the Australian Government dated Mar. 24, 2025 (6 Pages).
Singapore Office Action dated Jul. 28, 2025 for Singapore Patent Application No. 10201900302S (4 Pages).

* cited by examiner

NEEDLE GUIDE ASSEMBLY AND METHOD OF OPERATING THE SAME

CROSS-REFERENCE TO RELATED APPLICATIONS

This application is a 371 U.S. National Stage of International Application No. PCT/SG2019/050585, filed on Nov. 28, 2019, which claims priority to Singaporean Application No. 10201900302S filed on Jan. 11, 2019. The entire disclosures of the above applications are incorporated herein by reference.

FIELD OF INVENTION

The present invention relates broadly, but not exclusively, to a needle guide assembly and to a method of operating a needle guide assembly.

BACKGROUND

Many existing and emergent cancer therapy modalities involve the removal of cancerous lesions by ablation or radiotherapy. Among these, a few techniques—such as cryotherapy, laser ablation, irreversible electroporation (IRE), and brachytherapy—involve the insertion of needles or needle-shaped devices such as probes and introducers (henceforth all referred to as 'needles' for simplicity) to the target area.

In such procedures, positional guidance of the needle is necessary in order to ensure that the cancerous lesion is targeted and removed, and that healthy tissues are largely preserved. This can be achieved by means of an externally positioned needle guide that determines the trajectory of the needle passing through.

Conventional methods to guide a needle have several drawbacks. For example, the widely used brachytherapy template grid provides a grid of parallel needle guide channels, spaced apart at regular intervals. This means it does not provide the option of adjusting the angle of each needle, and insertion positions are limited to discrete points. Another commercially available biopsy needle guide, on the other hand, permits full positional control as it is robotically controlled in 5 degrees of freedom. However, it does not allow the insertion of multiple needles in a single procedure, such that at a single instant there are multiple needles in the patient's body. This is because the single needle guide is a closed channel, so if a needle has been inserted through it, it cannot move to the next position.

A need therefore exists to provide a needle guide that can address at least one of the above problems.

SUMMARY

An aspect of the present invention provides a needle guide assembly comprising a needle guide body comprising at least two separable portions; and a controller communicatively coupled to the needle guide body; wherein the needle guide body is operable by the controller to actuate between a closed configuration and an open configuration, wherein in the closed configuration, the at least two portions combine to define a channel therethrough for receiving a needle, and wherein in the open configuration, the at least two portions separate to release the received needle from the channel.

The channel may comprise a proximal end and a distal end, and the needle may be configured to be received at the proximal end and inserted through the channel toward the distal end.

An axis of the channel may be aligned in use with a needle insertion site adjacent the distal end, and the needle guide body may be pivotable about distal end.

The needle guide body may be movable to a next needle insertion site based on at least one parameter determined by the controller. The at least one parameter may comprise at least one of relative positions between consecutive needle insertion sites and needle diameter.

The assembly may further comprise an articulated arm mechanically connected to the needle guide body and communicatively coupled to the controller, for displacing the needle guide body based on instructions from the controller.

The at least two portions may be configured to move angularly relative to each other between the open and closed configurations. Alternatively or in addition, the at least two portions may be configured to move translationally relative to each other between the open and closed configurations.

Another aspect of the present invention provides an automated method of operating a needle guide assembly, the method comprising identifying a needle insertion site; moving a needle guide body of the needle guide assembly to the needle insertion site, the needle guide body comprising at least two separable portions operable between an open configuration and closed configuration; actuating the at least two portions to the closed configuration, the at least two portions defining a channel therethrough in the closed configuration; aligning an axis of the channel with the needle insertion site such that the axis has a predetermined angular orientation; and upon completion of needle insertion, actuating the at least two portions to the open configuration.

Aligning an axis of the channel with the needle insertion site may comprise pivoting the needle guide body about the distal end.

The method may further comprise moving the needle guide body to a next needle insertion site. Moving the needle guide body to the next needle insertion site may comprise controlling the needle guide body based on at least one parameter of relative positions between consecutive needle insertion sites and needle diameter.

Actuating the at least two portions may comprise moving the at least two portions angularly relative to each other. Alternatively or in addition, actuating the at least two portions may comprise moving the at least two portions translationally relative to each other.

Displacement of the needle guide body may be effected using an articulated arm.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

The inventors have noted that, to be effective in guiding needles for cancer therapy, the needle guide should preferably combine two characteristics. Firstly, it should provide the flexibility of having its position and angle independently controlled. This helps to permit higher resolution and accuracy in targeting the lesion, for example, in focal therapy where the index lesion which is typically targeted has a small volume of >0.5 cc to 1.3 cc, and a margin of 3-5 mm around it is required. Secondly, the needle guide should facilitate the insertion of multiple needles per procedure, as is the case with cryotherapy, IRE and brachytherapy.

The present disclosure provides a robotically controlled needle guide that permits the release of needles inserted through it and facilitates positional control of multiple needles.

Figure 1:
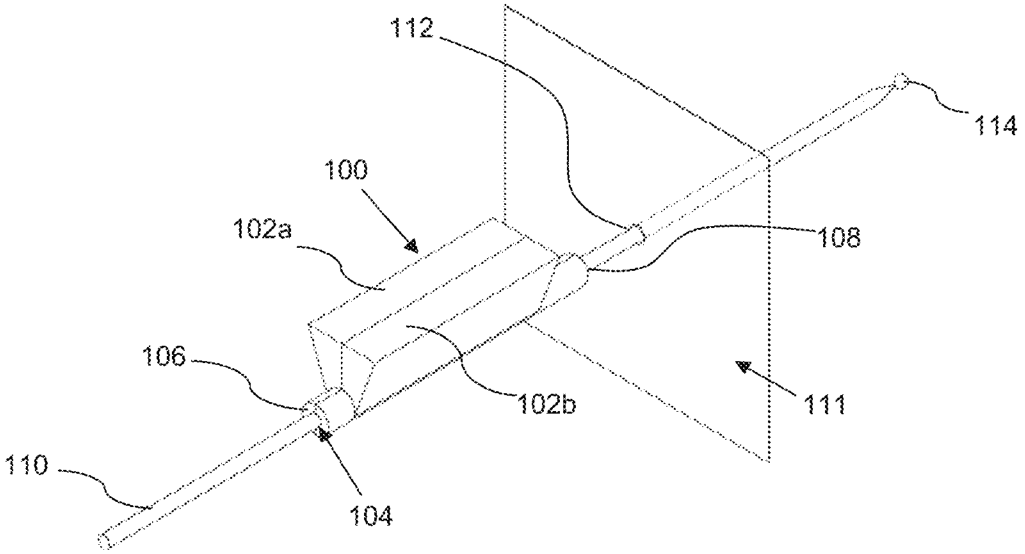
FIG. 1 shows a schematic diagram illustrating a needle guide body of a needle guide assembly according to an example embodiment.

FIG. 1 shows a schematic diagram illustrating a needle guide body 100 of a needle guide assembly according to an example embodiment. The needle guide body 100 includes at least two separable portions which are operable between an open configuration and closed configuration. In FIG. 1, two portions 102*a*, 102*b* are shown in the closed configuration but it will be appreciated that the needle guide body 100 can be made of more than two portions in alternate embodiments. Relative movement of the portions 102*a*, 102*b* between the open and closed configurations can be translational, angular, or a combination of both. For example, in one implementation, each portion 102*a*, 102*b* may be actuated by a respective motor (not shown in FIG. 1) to open/close in a hinge-like motion. In the open configuration, a slot or opening is formed between the portions 102*a*, 102*b*.

As shown in FIG. 1, in the closed configuration, the at least two portions 102*a*, 102*b* define a straight channel 104 running through the at least two portions 102*a*, 102*b*. For example, the channel 104 is formed by respective elongated grooves on the at least two portions 102*a*, 102*b*. The channel 104 has a proximal end 106 and a distal end 108. In use, the proximal end 106 is configured to receive a needle 110 which can be inserted through the channel 104 toward the distal end 108 before exiting the channel 104 from the distal end 108. In other words, the channel 104 serves to determine the trajectory of the needle 110 inserted through it.

For example, an axis of the channel 104 can be aligned with a needle insertion site 112 which is near or adjacent the distal end 108. The needle 110 is then inserted through the channel 104 such that the needle 110 passes through a skin 111 at the needle insertion site 112 and strikes a target 114. Further, the needle guide body 100 including the inserted needle 110 is pivotable about the distal end 108 to facilitate adjustment of the angular orientation of the needle 110 before or during the insertion procedure.

The cross-sectional size of the channel 104 in the example embodiments is configured to be slightly larger than the cross-sectional size of needle 110 to allow a relative smooth insertion of the needle 110 through the channel 104 while substantially constraining the angular orientation of the needle 110 to that of the channel 104. For example, if the needle 110 has a circular cross-section, the channel 104 may also have a circular cross-section of slightly larger diameter when the at least two portions 102*a*, 102*b* are fully closed. When a larger needle is to be used, the cross-sectional size of the channel 104 can be adapted accordingly.

Figure 2:
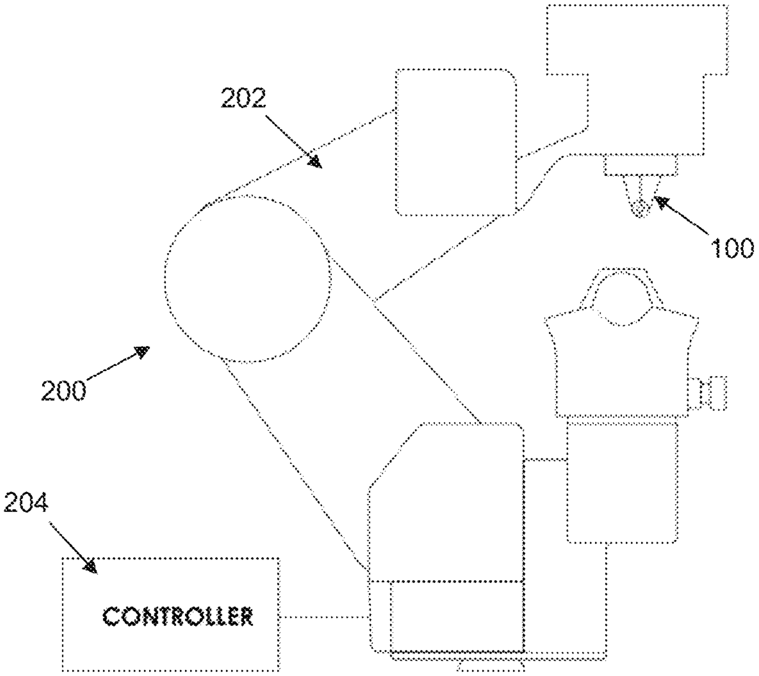
FIG. 2 shows a schematic diagram illustrating a needle guide assembly including the needle guide body of FIG. 1 according to an example embodiment.
Figure 3:
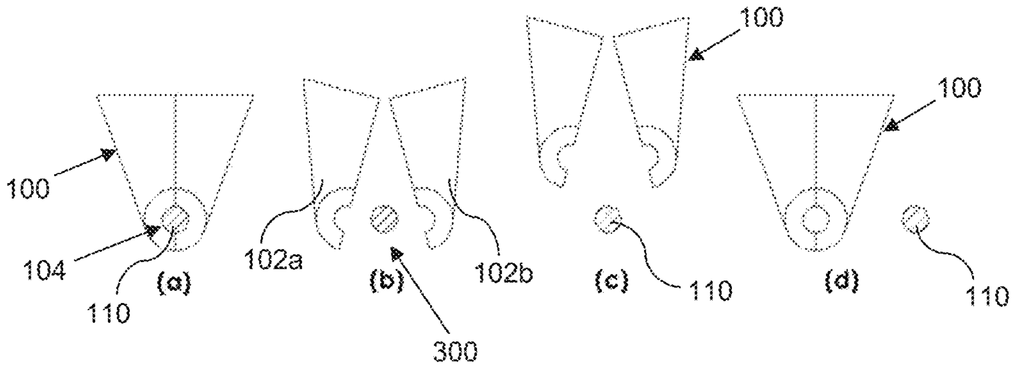
FIGS. 3*a*-3*d* show schematic diagrams illustrating example operations of the needle guide assembly of FIG. 2.

FIG. 2 shows a schematic diagram illustrating a needle guide assembly 200 including the needle guide body 100 of FIG. 1 according to an example embodiment. In this example, the needle guide body 100 is mechanically connected to a robotic or articulated arm 202 having multiple degrees of freedom such that displacement of the needle guide body 100 can be effected by the articulated arm 202. The robotic or articulated arm 202 and needle guide body 100 are communicatively coupled to a controller 204 (or computer system) which receives input relating to the needle insertion procedure and controls the arm 202 and needle guide body 100 accordingly.

FIGS. 3*a*-3*d* show schematic diagrams illustrating example operations of the needle guide assembly 200 of FIG. 2. During a needle insertion procedure, the needle guide body 100 is moved into position such that the needle tip will end up at the needle insertion site 112, as described above with reference to FIG. 1. The treatment needle 110 is then inserted by the doctor through the channel 104 of the body 100 (see FIG. 3*a*). After the needle 110 has been inserted to the desired position (e.g. through a predetermined insertion depth), the at least two portions 102*a*, 102*b* are actuated to the open configuration, forming a slot 300 larger than the diameter of the needle 110 (see FIG. 3*b*). The body 100 is then moved away, e.g. opposite to the direction of the slot 300, such that the needle 110 passes through the slot 300 and is left behind (see FIG. 3*c*). For the next needle, the body 100 is closed and moved to the next position (see FIG. 3*d*). The process of needle insertion and release is then repeated.

In the above example of FIGS. 3*a*-3*d*, the needle guide body 100 is moved substantially laterally from one needle insertion site to the next needle insertion site based on a sequence or algorithm determined by the controller 204 (FIG. 2). For example, the sequence is such that the amount of movement is minimised, or collision between the needle guide body 100 and inserted needles is avoided. However, it will be appreciated that different forms of movements can be applied in alternate embodiments. For example, the body 100 can be drawn back to achieve clearance from the needle before being moved to the next needle insertion site. Parameters that may be considered to optimise the path of the body 100 between needle insertion sites include, but are not limited to, relative positions between consecutive needle insertion sites, and needle diameter.

Figure 4:
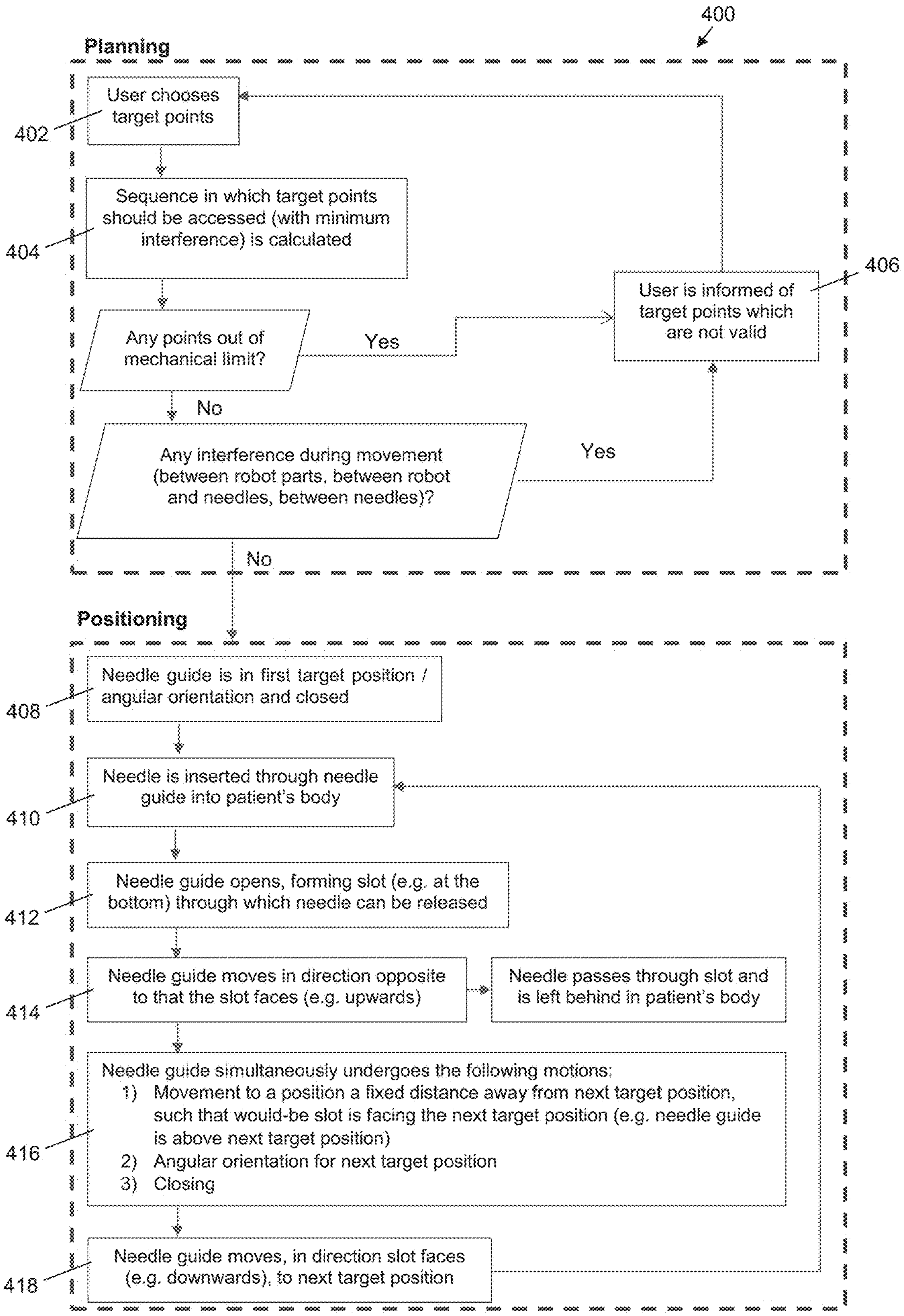
FIG. 4 shows a detailed flow chart illustrating operations of a needle guide assembly according to a non-limiting implementation.

FIG. 4 shows a detailed flow chart 400 illustrating operations of a needle guide assembly as described above with reference to FIGS. 1-2, according to a non-limiting implementation. The operations are divided mainly into a planning stage and a positioning stage. In the planning stage, step 402 involves a user (e.g. a urologist) choosing target points or needle insertion sites. Alternatively or in addition, this step may be performed with the help of artificial intelligence. Next, at step 404, the sequence in which target points should be accessed is calculated, e.g. based on the requirement of minimum interference. If there are points outside of the mechanical limit of the articulated arm 202 and/or needle guide body 100, at step 406, the user is informed of the target points which are not valid so that the user can adjust the choices. Further, even if no points are out of the mechanical limit, if it is determined that there will be interference during movement, e.g. between robot parts or between robot and needles, the user is similarly informed of the target points which are not valid.

On the other hand, if there is no interference, the process moves to the positioning stage where, at step 408, the needle guide body 100 is at the first needle insertion site and at the desired angular orientation, with the portions 102*a*, 102*b* forming the needle guide body 100 in the closed configuration. Next, at step 410, the needle 110 is inserted by the user through the channel 104 such that the needle 110 travels by a predetermined insertion depth from the first needle insertion site. The portions 102*a*, 102*b* forming the needle guide body 100 are then opened, at step 412, thereby forming a slot through which the needle can be released. Then, at step 414, the body 100 moves in a direction away from the needle 110 such that the needle passes through the slot and is left behind.

Before moving to the next target position, which is aligned with the next needle insertion site, the needle guide body 100 simultaneously undergoes several motions at step 416, including moving to a position a fixed distance away from the next target position, such that the slot to be formed by the portions 102*a*, 102*b* is facing and approximately parallel to the next target position, aligning with the next target position based on a desired angular orientation, and closing the portions 102*a*, 102*b*. Step 418 involves moving the body 100 in the direction the slot faces, to the next target position. There, the steps 410-416 as described above can be repeated.

In the example embodiments, the position of the slot (relative to the channel) is fixed for the needle guide body. For example, with reference to the top plan view in FIGS. 3*a*-3*d*, the slot is below the channel. As implemented, the position of the slot can be determined by how the needle guide body opens in its hinge-like motion. Hence, if the slot is formed at the bottom of the needle guide body, then the needle guide body will be moved to above the next target position. If the slot is at the right of the needle guide body, then the needle guide body will be moved to the left of the next target position.

As described above, many or all of the operations of needle guide assembly can be automated based on instructions from a controller or computer system, and performed by a robot. This can improve accuracy and repeatability. Also, the same needle guide assembly can be used for multiple needle insertions, in an efficient manner.

Figure 5:
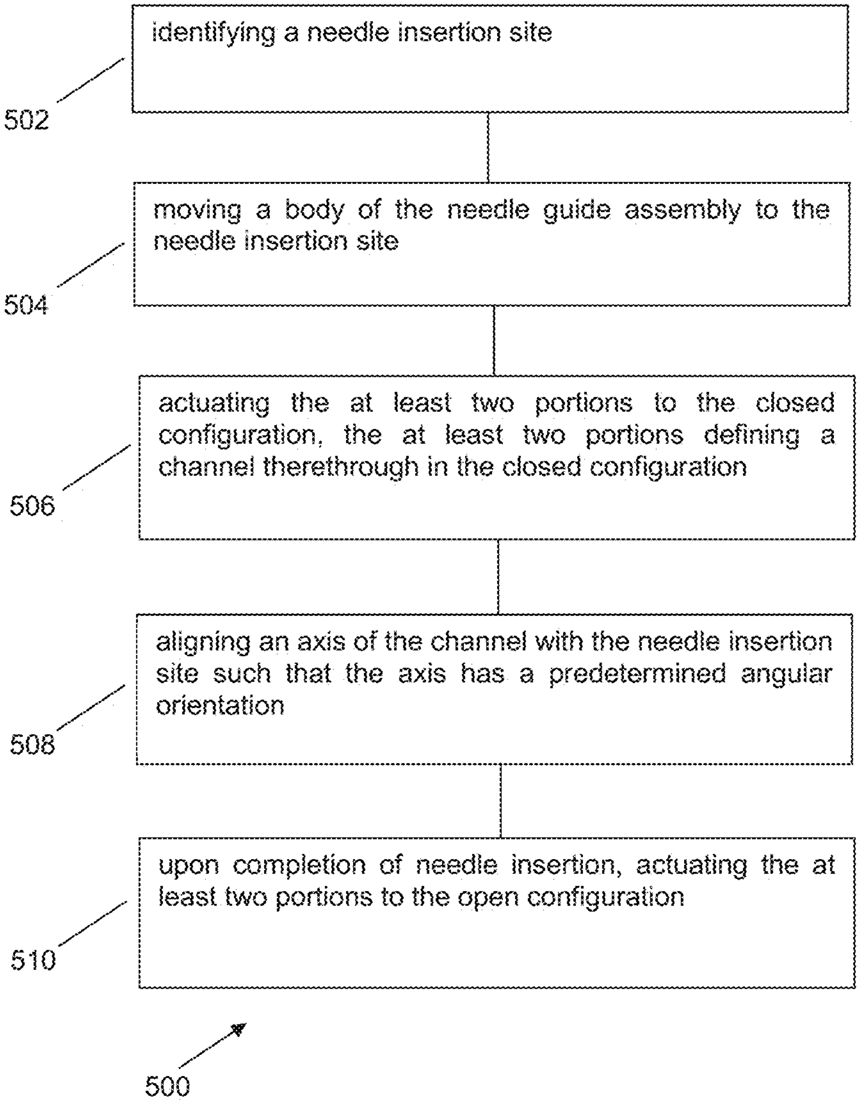
FIG. 5 shows a flow chart illustrating an automated method of operating a needle guide assembly according to an example embodiment.

FIG. 5 shows a flow chart 500 illustrating an automated method of operating a needle guide assembly according to an example embodiment. At step 502, a needle insertion site is identified. At step 504, a needle guide body of the needle guide assembly is moved to the needle insertion site. The needle guide body includes at least two separable portions operable between an open configuration and closed configuration. At step 506, the at least two portions are actuated to the closed configuration, the at least two portions defining a channel therethrough in the closed configuration. At step 508, an axis of the channel is aligned with the needle insertion site such that the axis has a predetermined angular orientation. At step 510, upon completion of needle insertion, the at least two portions are actuated to the open configuration.

It will be appreciated by a person skilled in the art that numerous variations and/or modifications may be made to the present invention as shown in the specific embodiments without departing from the scope of the invention as broadly described. For example, with reference to FIG. 5, the steps are not necessarily performed in the sequence as described. The present embodiments are, therefore, to be considered in all respects to be illustrative and not restrictive.

The invention claimed is:

1. An automated needle guide assembly for inserting multiple needles during a single procedure, the needle guide assembly comprising:

a needle guide body comprising at least two separable portions; and a controller communicatively coupled to the needle guide body;

wherein the at least two separable portions of the needle guide body are operable by the controller, by controlling respective motors, to actuate between a closed configuration and an open configuration, wherein in the closed configuration, the at least two separable portions combine to define a channel therethrough for receiving a needle, and wherein in the open configuration, the at least two separable portions separate to release the received needle from the channel, wherein the channel comprises a proximal end and a distal end, and wherein the needle is configured to be received at the proximal end and inserted through the channel toward the distal end;

wherein an axis of the channel is aligned in use with a needle insertion site adjacent to the distal end, and wherein the needle guide body is pivotable about the distal end; and wherein the needle guide assembly further comprises an articulated arm mechanically connected to the needle guide body and communicatively coupled to the controller, for displacing the needle guide body based on instructions from the controller, and wherein the controller is configured to control the articulated arm to laterally move the needle guide body to a next needle insertion site based on an automated sequence determined by the controller that minimizes movement and avoids collision between the needle guide body and previously inserted needles.

2. The assembly as claimed in claim 1, wherein the needle guide body is movable laterally to the next needle insertion site based on at least one parameter determined by the controller.

3. The assembly as claimed in claim 2, wherein the at least one parameter comprises relative positions between consecutive needle insertion sites.

4. The assembly as claimed in claim 1, wherein the articulated arm comprises a plurality of sequentially arranged sections that pivot relative to each other, for moving the needle guide body based on instructions from the controller.

5. The assembly as claimed in claim 1, wherein the at least two separable portions are configured to move angularly relative to each other between the open and closed configurations.

6. The assembly as claimed in claim 1, wherein the at least two separable portions are configured to move translationally relative to each other in a rectilinear motion between the open and closed configurations.

7. The assembly as claimed in claim 1, wherein the at least two separable portions comprise two separable portions connected by a hinge, and wherein the hinge comprises a hinge axis parallel to the axis of the channel.

8. The assembly as claimed in claim 7, wherein each of the two separable portions comprises a cross-section perpendicular to the axis of the channel, wherein the cross-section tapers from a wider first end adjacent to the hinge to a narrower second end adjacent to the channel when the needle guide body is in the closed configuration.

9. The assembly as claimed in claim 1, wherein the needle guide body is movable to a position a fixed distance away from the next needle insertion site such that the channel formed by the two separable portions is facing and approximately parallel to the next needle insertion site.

* * * * *